(12) United States Patent
Barr

(10) Patent No.: US 8,157,812 B2
(45) Date of Patent: Apr. 17, 2012

(54) SLOTTED DEPLOYMENT DEVICE

(75) Inventor: Aaron P. Barr, Fishers, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 322 days.

(21) Appl. No.: 12/208,188

(22) Filed: Sep. 10, 2008

(65) Prior Publication Data

US 2010/0063458 A1   Mar. 11, 2010

(51) Int. Cl.
*A61B 17/00*   (2006.01)
(52) U.S. Cl. .......................................... 606/116; 600/564
(58) Field of Classification Search ................... 606/116, 606/151, 191, 194, 185; 600/414, 420, 426, 600/431, 434, 564; 604/174, 264, 116, 506
See application file for complete search history.

(56) References Cited

U.S. PATENT DOCUMENTS

| | | | |
|---|---|---|---|
| 5,505,210 A | 4/1996 | Clement | |
| 5,549,595 A | 8/1996 | Freitas | |
| 6,220,248 B1 | 4/2001 | Voegele et al. | |
| 7,037,321 B2 | 5/2006 | Sachdeva et al. | |
| 7,044,958 B2 * | 5/2006 | Douk et al. | 606/200 |
| 7,841,990 B2 | 11/2010 | Mark et al. | |
| 2005/0277918 A1 | 12/2005 | Shah et al. | |
| 2008/0228164 A1 * | 9/2008 | Nicoson et al. | 604/506 |
| 2009/0069819 A1 * | 3/2009 | Barr | 606/116 |

FOREIGN PATENT DOCUMENTS

WO   WO 2007035798   3/2007

OTHER PUBLICATIONS

Amendment in Response to Non-Final Office Action mailed Jun. 16, 2011, for U.S. Appl. No. 11/852,913, submitted on Nov. 16, 2011 (14 pages).
Non-Final Office Action for U.S. Appl. No. 11/852,913, mailed Jun. 16, 2011 (9 pages).
PCT International Search Report and Written Opinion for PCT/US2008/075563, Applicant Suros Surgical Systems, Inc., Forms PCT/ISA/210, 220, and 237, dated Nov. 7, 2008 (16 pages).

* cited by examiner

*Primary Examiner* — Victor Nguyen
(74) *Attorney, Agent, or Firm* — Vista IP Law Group LLP

(57) ABSTRACT

A delivery cannula for a site marker deployment device is disclosed. The delivery cannula includes a cannula having a tubular sidewall and at least one slot intersecting through the side wall. Each slot is sized to have a predetermined width so as to be configured to receive at least one filament of a site marker. When the site marker is inserted into the delivery cannula, at least a portion of the filament extends outwardly from the cannula and through the slot. A deployment system is also disclosed.

9 Claims, 3 Drawing Sheets

SLOTTED DEPLOYMENT DEVICE

TECHNICAL FIELD

The present disclosure relates generally to site markers for breast biopsy procedures. More specifically, the present disclosure relates to a deployment device for delivering site markers to a predetermined location within a patient.

BACKGROUND

In the diagnosis and treatment of breast cancer, it is often necessary to perform a biopsy to remove tissue samples from a suspicious mass. The suspicious mass is typically discovered during a preliminary examination involving visual examination, palpation, X-ray, magnetic resonance imaging (MRI), ultrasound imaging or other detection means.

When a suspicious mass is detected, a sample is taken by biopsy, and then tested to determine whether the mass is malignant or benign. This biopsy procedure can be performed by an open surgical technique, or through the use of a specialized biopsy instrument. To minimize surgical intrusion, a small specialized instrument such as a biopsy needle is inserted in the breast while the position of the needle is monitored using fluoroscopy, ultrasonic imaging, X-rays, MRI or other suitable imaging techniques.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, and the original features of the tissue may have been removed or altered by the biopsy, it is desirable to insert at least one site marker into the surgical cavity to serve as a landmark for future identification of the location of the lesion.

Commonly assigned application U.S. patent application Ser. No. 11/242,334 discloses a variety of markers that use expandable filament portions to 'hold' a site marker in place within a biopsy cavity. That is, a site marker may include a bio-absorbable filament portion, such as a suture, with a marker attached thereto, where the marker is visible under multiple modalities and the suture will inhibit migration of the marker within the biopsy cavity. The filament portions of these structures typically define a site marker diameter that is greater than the outer diameter of a delivery cannula. In one embodiment, to insert a site marker within a biopsy site, the site marker is compressed (at least partially elastically deformed) to a dimension that will permit the site marker to be interposed within the delivery cannula. The site marker is interposed within an opening of the delivery cannula, and the site marker and cannula are sterilized. When in use, the cannula is inserted within a biopsy canal such that the opening of the delivery cannula is within the biopsy site, and the site marker is deployed into the biopsy site. Once deployed, the site marker will expand as the filament portions exit the cannula in reaction to the elastic deformation. The site marker will expand until the elastic deformation is eliminated or portions of the site marker interfere with the inside portions of the biopsy cavity.

The site marker and cannula must be sterile in order to be placed into a biopsy cavity. However, the elastically deformed filament portions, or other materials, plastically deform within the cannula due to the heat of sterilization (essentially converting some of the elastic deformation to plastic deformation). Therefore, the filament portions may not properly expand upon exiting the delivery cannula. Lack of sufficient expansion may permit migration within the biopsy cavity.

Accordingly, there is a need for site markers and delivery systems that are compatible with sterilization and packaging techniques.

SUMMARY

A delivery cannula for a site marker deployment device is disclosed. The delivery cannula comprises a cannula having a tubular sidewall and at least one slot intersecting through the side wall. Each slot is sized to have a predetermined width so as to be configured to receive at least one filament of a site marker. When the site marker is inserted into the delivery cannula, at least a portion of the filament extends outwardly from the cannula and through the slot. A deployment system is also disclosed.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are not intended to be exhaustive or otherwise limit or restrict the claims to the precise forms and configurations shown in the drawings and disclosed in the following detailed description.

DETAILED DESCRIPTION

Figure 1:
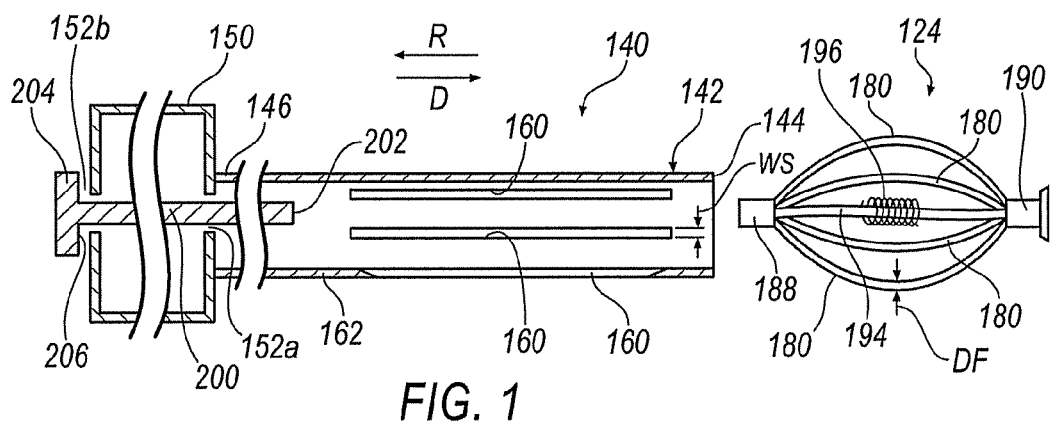
FIG. 1 is an exploded partially sectioned side view of a site marker deployment system.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present invention. Further, the descriptions set forth herein are not intended to be exhaustive or otherwise limit or restrict the claims to the precise forms and configurations shown in the drawings and disclosed in the following detailed description.

Turning now to the drawings and in particular to FIG. 1, an exemplary deployment device 140 is disclosed. In the arrangement of FIG. 1, the deployment device 140 includes a delivery cannula 142 and a site marker 124. The delivery cannula 142 extends from a distal end 144 to a proximal end 146. The deployment device 140 also includes a gripping portion 150 attached to the proximal end 146 of the delivery cannula 142. The gripping portion 150 includes apertures 152a, 152b that are in communication with the delivery cannula 142. A push rod 200 is inserted through apertures 152*a*, 152*b* and is at least partially interposed within the delivery cannula 142. The push rod 200 is defined by a distal end 202 and a proximal end 206. A push rod handle 204 is located at the proximal end 206 of the push rod 200.

Figure 2:
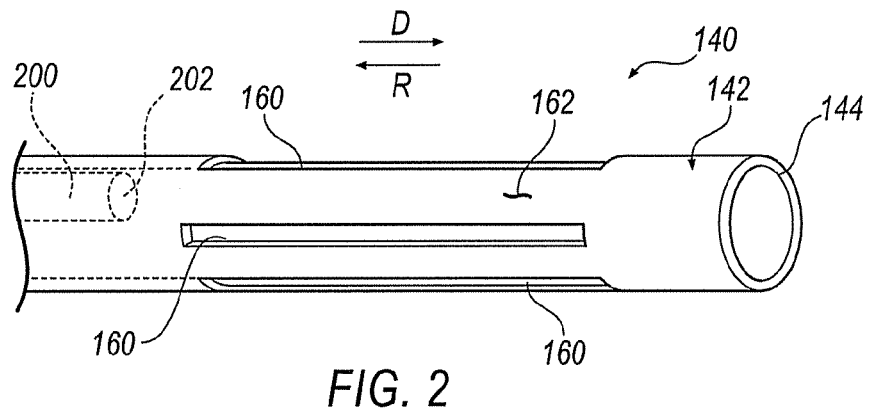
FIG. 2 is a partial perspective view of a portion of the site marker deployment system of FIG. 1.

As best seen in FIGS. 1-2, the delivery cannula 142 includes at least one slot 160 interposed between the distal end 144 of the delivery cannula 142 and the proximal end 146 of the delivery cannula 142. The at least one slot 160 extends through the thickness of a tubular sidewall 162 of the delivery cannula 142 and is configured with a predetermined slot width WS (to be explained in further detail below.

In those embodiments that include more than one slot 160, the slots 160 are generally circumferentially spaced along the sidewall 162. In one exemplary arrangement, the slots 160 are arranged equidistance from one another. Further, as illustrated in FIGS. 1-2, the slots 160 do not intersect the distal cannula end 144. It should be noted that while FIG. 1 illustrates three slots 160 through the sidewall 162, any number of slots 160 may be included.

Figure 5:
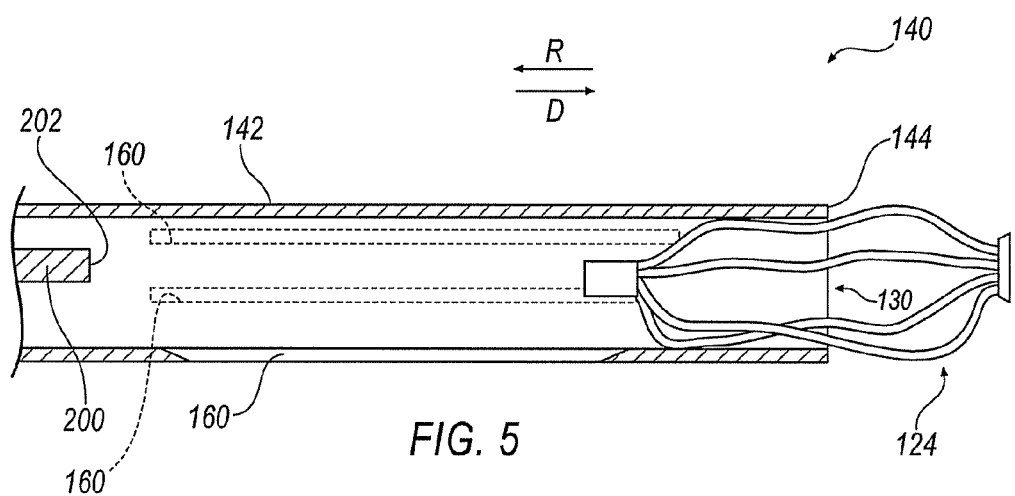
FIG. 5 is a partially sectioned side view of the site marker and the deployment device of FIG. 1.
Figure 6:
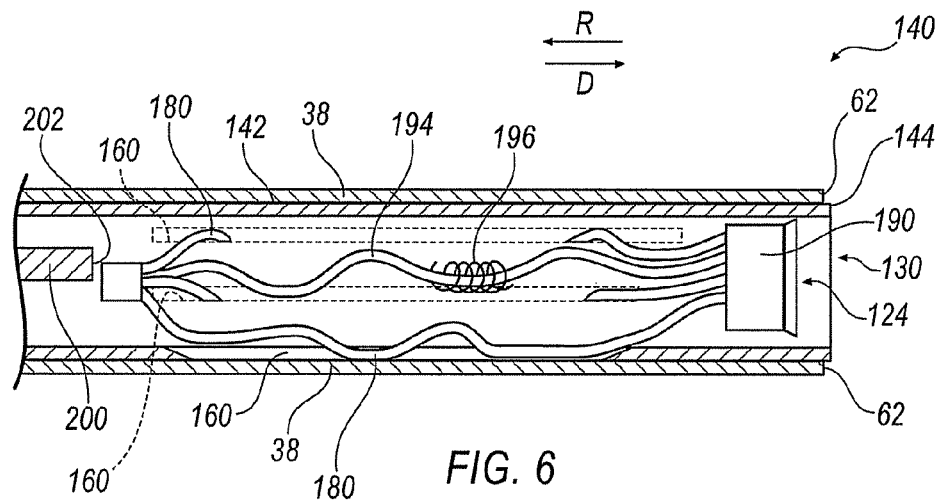
FIG. 6 is a partially sectioned side view of the site marker and the site marker deployment device of FIG. 1.

As described above, the deployment device 140 may be used with the site marker 124. The site marker 124 is selectively configurable between a first deployed configuration (FIG. 1) and a first retracted configuration (FIGS. 5 and 6). Indeed, site marker 124 is elastically deformable such that the site marker 124 may be interposed through the distal opening 130 to move the site marker 124 into the retracted configuration (see, e.g., FIG. 5). As best seen in FIG. 1, the site marker 124 includes a plurality of generally elongated filament members 180 and at least one end connection 190. Each of the filament members 180 are defined by a filament diameter DF that is at least slightly less than the slot width WS.

The filament members 180 are elastically deformable such that the site marker 124 may be compressed into the marker retracted configuration and interposed within the delivery cannula 142 by pushing or pulling the site marker 124 in the R direction, so as to position the site marker 124 within a sterilization configuration (to be described below). As described above, the site marker 124 is elastically deformable to the marker retracted configuration such that the site marker 124 may be inserted into the cannula 142 prior to sterilization and deployment.

In one exemplary arrangement, each of the filament members 180 extends between a first end connection 188 and the second end connection 190. In the embodiment illustrated, one filament member 194 is configured to be shorter than the remaining filament members 180. Thus configured, the filament member 194 will remain generally linear while the filament members 180 are resiliently curved. In addition, filament member 194 may be provided with a marker element, or a permanent marker 196 attached thereto. It is understood that filament member 194 and the permanent marker 196 may be omitted. It should also be noted that while FIG. 1 illustrates the site marker 124 as including four curved filament members 180, any number of filament members 180 may be provided without departing from the disclosure.

As stated above, at least one of the filament members 180 are selectively configurable between a first deployed configuration (FIG. 1) and a first retracted configuration (FIG. 5). That is, the site marker 124 is configurable between the first deployed configuration (FIG. 1) and the first retracted configuration (FIG. 5) as at least one of the filament members 180 are deformed, while not all filament members 180 need be deformed to deform the site marker 124 between the first deployed configuration and the first retracted configuration. In the first deployed configuration (FIG. 1) the site marker 124 can not enter the delivery cannula 142 as the diameter of the site marker 124 is greater than the diameter of the distal end 144 of the delivery cannula 142. In the first retracted configuration the site marker 124 is deformed so as to permit the site marker 124 to be interposed within the delivery cannula 142.

Figure 3:
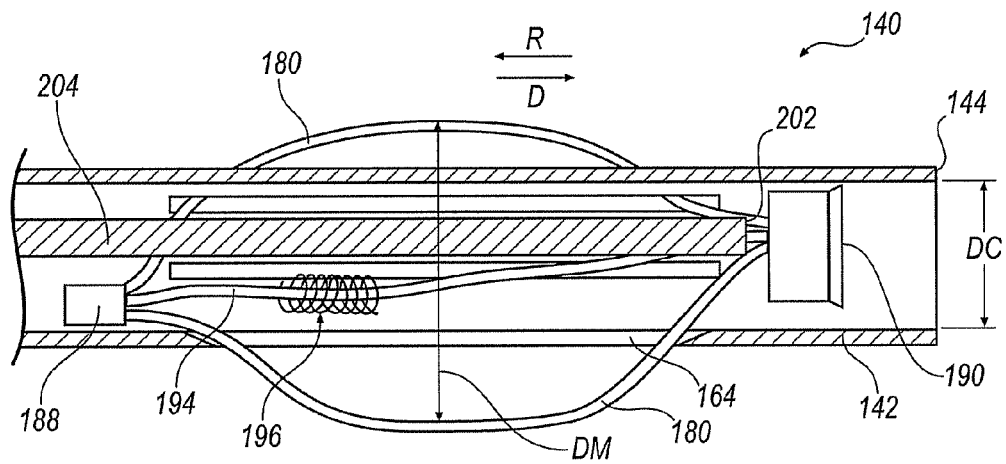
FIG. 3 is a partially sectioned side view of a portion of the site marker positioned within the site marker deployment device of FIG. 1.
Figure 4:
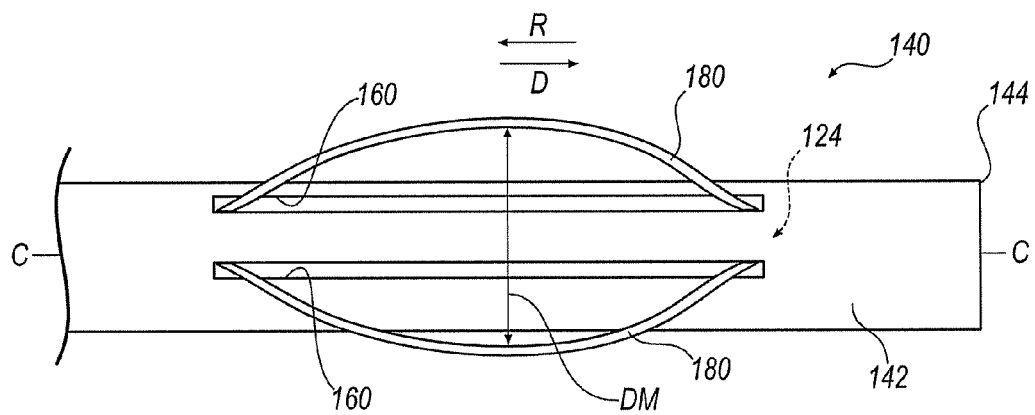
FIG. 4 is a side view of the site marker deployment device of FIG. 3.

FIGS. 3 and 4, illustrate the sterilization configuration of the site marker 124. In the sterilization configuration, one or more filament members 180 extends through at least one corresponding slot 160. In other words, not every filament member 180 need extend through a corresponding slot 160, just at least one. Filament member 194 remains within the delivery cannula 142 due to its shorter length as opposed to filament members 180. Thus positioned, the site marker 124 may be retained at least partially within the delivery cannula 142 while permitting at least a portion of the filament members 180 to define a site marker dimension that is greater than the diameter of the delivery cannula 142.

While in the sterilization configuration, the site marker 124 may be sterilized while the filament members 180 are deformed less than the deformation associated with the entire site marker 124 being wholly interposed within the inner cannula 142 (as shown in FIG. 5). The delivery device 140 may be supplied in the sterilization configuration of FIGS. 3 and 4 and the deployment device 140 may then be sterilized prior to deployment of the site marker 124, or, alternatively, the system may be sterilized in the sterilization configuration of FIGS. 3 and 4 and supplied and/or stored in this configuration awaiting deployment at a later time.

Deployment of the site marker 124 will now be described. In operation, deployment device 140 is typically used with an introducer cannula 38 that defines an inner lumen therein. An example of an introducer cannula 38 may be found in commonly owned U.S. Pat. No. 7,347,829, entitled, INTRODUCTION SYSTEM FOR MINIMALLY INVASIVE SURGICAL INSTRUMENTS, the contents of which are herein incorporated by reference in its entirety. The introducer cannula 38 is typically already inserted into the patient so as to form a pathway in the patient's body, prior to utilizing a site marker deployment device 140. Thus, the delivery cannula 142 of the deployment device 140 is inserted into the lumen of the introducer cannula 38. During insertion of the delivery cannula 142 into the introducer cannula 38 (FIG. 6), the filament members 180 will interfere with a distal end 62 of the introducer cannula 38 in order to urge the filament members 180 inwardly toward a central axis extending through the delivery cannula 142. This action will also cause the filament members 180 to compress back through the slots 160 so as to be ready for deployment. It is also contemplated that the deployment device 140 may be inserted into a cannula of a biopsy device, rather than an introducer cannula 38 or in addition to an introducer cannula 38.

When the delivery cannula 142 is interposed within the introducer cannula 38, the push rod 200 may be activated to deploy the site marker 124 into the patient. For example, as the push rod 200 contacts a portion of the site marker 124 and advanced toward the distal end 144, the site marker 124 is moved generally in the direction of the arrow D until the site marker 124 is deployed into the body. Once deployed, the site marker 124 will spring into the deployment configuration (due to the elastic deformation) into the deployed configuration having a size and shape defined by the biopsy cavity such that the site marker is easily visible under various imaging modalities, while inhibiting migration of the site marker 124, as well as preventing "drag out" of the site marker, i.e., causing the site marker to reenter the delivery cannula 142.

In general, the site markers described herein are made from biocompatible materials such as, but not limited to, titanium, stainless steel, and platinum. These materials have appropriate densities for radiographic imaging, appropriate surface characteristics for ultrasonic imaging, and appropriate magnetic characteristics for magnetic resonance imaging, as well as other imaging modalities. The site markers are preferably made from titanium; however, it is understood that any suitable biocompatible material may be used. Commonly owned U.S. patent application Ser. Nos. 11/242,334, 10/964,087, and 11/561,919, the contents of which are herein incorporated by reference in their entireties, disclose a variety of site markers that may be used in conjunction with the deployment device 140.

Although the steps of the method of deploying the site markers described herein are listed in a preferred order, the steps may be performed in differing orders or combined such that one operation may perform multiple steps. Furthermore, a step or steps may be initiated before another step or steps are completed, or a step or steps may be initiated and completed after initiation and before completion of (during the performance of) other steps.

While the present invention has been particularly shown and described with reference to the foregoing preferred embodiments, it should be understood by those skilled in the art that various alternatives to the embodiments of the invention described herein may be employed in practicing the invention without departing from the spirit and scope of the invention as defined in the following claims. It is intended that the following claims define the scope of the invention embodiments within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiment is illustrative, and no single feature or element is essential to all possible combinations that may be claimed in this or a later application.

What is claimed is:

1. A site marker deployment system comprising:
   a deployment device having a delivery cannula and at least one slot; and
   a site marker including at least one generally elongated filament member selectively configurable between a first deployed configuration, wherein the site marker can not be interposed within the delivery cannula, and a second configuration, wherein the site marker is selectively interposed within the delivery cannula;
   wherein the delivery cannula is configured to selectively retain the site marker, such that at least a portion of the site marker is interposed within the delivery cannula and at least a portion of the at least one filament of the site marker extends into at least one slot in the delivery cannula, wherein the slot extends through the thickness of a sidewall of the delivery cannula.

2. The system of claim 1, further comprising a push rod at least partially interposed within the delivery cannula, wherein the site marker, when interposed within the delivery cannula, is selectively axially moved by movement of the push rod.

3. The system of claim 2, wherein the site marker further includes a plurality of filament members and the delivery cannula further includes a plurality of slots.

4. The system of claim 3, wherein the slots are spaced equidistant about a circumference of the delivery cannula.

5. The system of claim 4, wherein the slots are oriented so as to be generally parallel to a central axis extending through the delivery cannula.

6. The system of claim 3, wherein the site marker is defined, at least in part, by an end connection that connects the plurality of filament members together.

7. The system of claim 3, wherein of the filament members further includes a separate marker element secured thereto.

8. The system of claim 1, wherein (i) when the site marker is not interposed within the delivery cannula, at least a portion of the site marker expands to a deployed configuration where a dimension of the site marker measured generally normal to a generally central axis of the delivery cannula is greater than a diameter of the delivery cannula; and (ii) when the site marker is interposed within the delivery cannula, at least a portion of the site marker is deformed into a retracted configuration whereby a dimension of the site marker measured generally normal to the generally central axis of the delivery cannula is less than the diameter of the delivery cannula.

9. The system of claim 1, wherein the at least one filament extends through the slot and outwardly from the delivery cannula.

* * * * *